United States Patent [19]

Warner

[11] Patent Number: 4,933,509

[45] Date of Patent: Jun. 12, 1990

[54] METHOD OF ORTHO-ALKYLATING PHENOL

[75] Inventor: Gregory L. Warner, Schenectady, N.Y.

[73] Assignee: General Electric Company, Schenectady, N.Y.

[21] Appl. No.: 344,641

[22] Filed: Apr. 28, 1989

[51] Int. Cl.$^5$ .................. C07C 37/16; C07C 37/11
[52] U.S. Cl. .................. 568/804; 568/790; 568/794; 502/159
[58] Field of Search ............ 568/804, 789, 790, 794; 502/159

[56] References Cited

U.S. PATENT DOCUMENTS

| | | | |
|---|---|---|---|
| 3,962,126 | 6/1976 | Pecak | 502/159 |
| 3,972,836 | 8/1976 | Van Sorge | 568/804 |
| 4,041,085 | 8/1977 | Frabetti et al. | 568/804 |
| 4,100,207 | 7/1978 | Goodwin et al. | 568/804 |
| 4,454,357 | 6/1984 | Inone et al. | 568/804 |
| 4,503,272 | 3/1985 | Bennett Jr. | 568/804 |
| 4,528,407 | 7/1985 | Smith et al. | 568/804 |
| 4,547,480 | 10/1985 | Bennett Jr. | 502/159 |
| 4,554,266 | 11/1985 | Bennett et al. | 502/344 |

FOREIGN PATENT DOCUMENTS

| | | | |
|---|---|---|---|
| 0066836 | 7/1978 | Japan | 568/804 |
| 56-06393 | 2/1981 | Japan | 568/804 |

OTHER PUBLICATIONS

Silica Gels and Powders, p. 540.
R. I. Razouk and R. Su Mikhail, Surface Properties of Magnesium Oxide ID, Jul. 1959, vol. 63, pp. 1050-1053.
P. J. Anderson and P. L. Morgan, Effects of Water Vapour on Sintering of MgO, Jan. 7, 1964, pp. 930-937.

Primary Examiner—Werren B. Lone
Attorney, Agent, or Firm—William A. Teoli; James C. Davis, Jr.; William H. Pittman

[57] ABSTRACT

A method is provided for ortho-alkylating phenol by passing a mixture of phenol and methanol through a heated magnesium oxide catalyst. The magnesium oxide catalyst is made by calcining magnesium carbonate and thereafter further heating the calcined product in the presence of steam.

6 Claims, No Drawings

METHOD OF ORTHO-ALKYLATING PHENOL

BACKGROUND OF THE INVENTION

The present invention relates to a method for making 2,6-dimethylphenol, or 2,6-xylenol, by effecting reaction between phenol and methanol in the presence of a magnesium oxide catalyst. More particularly, the present invention relates to a method for minimizing the production of mesitol, or 2,4,6-trimethyl phenol, an odor causing waste, by employing a magnesium oxide catalyst which has been formed by calcining magnesium carbonate followed by heating the resulting magnesium oxide in the presence of steam until the surface area of the resulting product achieves a predetermined value.

Prior to the present invention, methods for making 2,6-xylenol were sought as it is a basic starting reactant for making high performance polyphenylene ethers. Various magnesium catalysts, such as formulations of magnesium carbonate and magnesium hydroxide, enhanced with manganese or copper additives have been used to improve catalyst selectivity with respect to 2,6-xylenol production as shown by U.S. Pat. Nos. 4,503,272 and 4,554,266. Enhanced magnesium oxide selectivity also is reported in U.S. Pat. No. 4,528,407, by employing a low calcination temperature. High magnesium oxide catalyst activity i.e. maintaining catalyst life as distinguished from catalyst selectivity which would minimize the production of unwanted by-products, is reported in U.S. Pat. Nos. 3,974,229 and 3,972,386 by exposing magnesium carbonate to methanol vapors during calcination. Experience has shown that a high proportion of 2,4,6-tri-methylphenol or "mesitol" can be formed as a result of over alkylation of the phenol ring when exposed to methanol vapors during calcination. There is further reported in U.S. Pat. No. 4,454,557 that high catalyst selectively can be achieved by pretreating a metal oxide catalyst with phenol. Experience has shown however, that adverse activity and selectivity can result when phenol is used on magnesium oxide prior to its employment as a phenol ortho alkylation catalyst.

It has been further reported in Japanese patent No. J56063932, that if a metallic salt, such as magnesium nitrate is blended with additional metal salts and heated at temperatures of 500° C. and steamed, improved selectivity is achieved when the resulting magnesium reaction product is used during the alkylation of phenol with methanol.

SUMMARY OF THE INVENTION

It would be desirable to provide a magnesium oxide catalyst for the ortho-alkylation of phenol utilizing a mixture of methanol and phenol which would minimize the production of mesitol. It also would be desirable to provide a magnesium oxide catalyst which would achieve a high degree of both catalyst activity and selectivity which would enhance the production of 2,6-xylenol without the excess formation of 2,4,6-trimethylphenol, and which did not require the use of catalyst promoters, such as manganese, copper based additives, or phenolic vapors.

The present invention is based on the discovery that a magnesium oxide catalyst exhibiting a high degree of activity and selectivity for the ortho-alkylation of phenols resulting from the reaction of methanol and phenol, can be made by initially calcining magnesium carbonate at a temperature in the range of about 350° C. to about 440° C. under a dry inert gas, such as flowing nitrogen, air, or a mixture of inert gas and a minor amount of oxygen, to convert the magnesium carbonate to magnesium oxide, and thereafter heating the magnesium oxide in the presence of steam until a predetermined surface area of the resulting magnesium oxide is achieved as a result of the agglomeration or sintering of the catalyst.

STATEMENT OF THE INVENTION

There is provided by the present invention, a method for ortho-alkylating phenol, which comprises, effecting reaction between methanol and phenol at a temperature in a range from 350° C. to 550° C. in the presence of a magnesium oxide catalyst, where there is used from 3 to 5 mols of methanol, per mol of phenol, and the magnesium oxide catalyst is the product obtained by (1) calcining magnesium carbonate at a temperature in the range from 350° C. to 440° C. under a dry gas stream, selected from the class consisting of air, an inert gas, and an inert gas mixture having up to about 21% oxygen by weight, until the magnesium carbonate is converted to magnesium oxide and, (2) heating the calcined product of (1) at a temperature from 350° C. to 550° C. in the presence of steam until the surface area of the resulting magnesium oxide product achieves a predetermined value.

The magnesium carbonate which can be used in the practice of the present invention can be more particularly described as magnesite, nesquehonite, landsfordite and other magnesium carbonate hydrates.

The calcination of the magnesium carbonate used in the practice of the invention, can be achieved in a metallic tubular fixed bed reactor. Magnesium carbonate, preferably in the form of pellets is incorporated into the metal tubes. A heat transfer medium such as a fluidized sand bath can be used to heat the reactor which can be made of 304L stainless steel. A calcination temperature in the range of 350° C. to 440° C. can be used. A dry inert gas, such as nitrogen, helium, or argon, or a dry oxygen containing gas such as air can be passed through the magnesium carbonate during the heating stage. Analysis of the effluent gas for residual carbon dioxide after a period of 6 to 48 hours, based on a gas hourly space velocity (GHSV) of 0.2–2.0 parts by weight of purge gas, per part of magnesium carbonate per hour, can be used to establish the termination of the calcination period.

At the termination of the calcination step, steam at a temperature of 350° C. to 550° C. and a pressure of 0 psig to 200 psig can be injected into the reactor over a period of from about 0.5 to about 48 hours. It has been found that treatment of surface of the magnesium oxide with steam at the aforementioned temperatures tends to agglomerate or sinter the magnesium oxide crystallites resulting from magnesium carbonate calcination. Through steam sintering, surface morphology is altered in such a way as to enhance selectivity while maintaining sufficient activity. A surface area of 100 $M^2/g$ to 200 $M^2/g$ can be achieved after 6 to 48 hours at the aforementioned temperatures to provide optimum activity and selectivity.

Phenol alkylation can be achieved by feeding a mixture of methanol and phenol through the sintered magnesium oxide at a temperature of from 350° C. to 550° C. and preferably 20° C. to 460° C. A liquid hourly space velocity (LHSV) of the feed mixture in proportions of methanol to phenol as previously defined, of from 1.5 to 2.5 parts by weight of feed mixture, per part by weight of magnesium carbonate per hour will provide effective results.

In order that those skilled in the art will be better able to practice the present invention, the following examples are given by way of illustration and not by way of limitation. All parts are by weight unless otherwise indicated.

EXAMPLE 1

There was charged, 280 parts of magnesium carbonate into a fixed bed tubular reactor. The magnesium carbonate was heated twenty-four hours at 380° C. under a dry gas mixture of nitrogen having 2% by weight of oxygen. The resulting calcined magnesium carbonate was divided into four equal parts. "Sample 1" (control) was not treated further. Samples 2 and 3 were further heated at 440° C. for twenty-four hours with steam which was prepared by introducing water into a heating medium at reactor temperatures prior to contacting the calcined magnesium carbonate.

Sample 2 was further heated for twenty-four hours under dry nitrogen, Sample 3 was not treated further. Sample 4 was not treated with steam but it was heated at 440° C. under dry nitrogen for a total of forty-eight hours.

The above four magnesium oxide samples were then evaluated for catalyst selectivity in a tubular fixed bed reactor. An aqueous feed mixture of methanol and phenol having 20% by weight water based on total feed and a ratio of about 4 mols of methanol, per mol of phenol was passed into a reactor through the magnesium oxide catalyst as described above, at a temperature of 440° C. and 25 psig. The liquid hourly space velocity (LHSV) was 2.0, per hour. After four days of passing the feed mixture through the magnesium oxide catalyst, the weight percent of the resulting phenolics was measured in the effluent stream. In determining selectivity to make 2,6 xylenol, several factors were considered such as the amount of phenol consumed less the amount of recyclable phenol and ortho cresol. In addition the following formula was used:

$$\text{Selectivity} = \frac{2,6 \text{ xylenol produced}}{2,6 \text{ xylenol} + \text{mesitol} + \text{other}} \times 100$$

The following results were obtained:

| | WEIGHT % OF PHENOLICS | | | |
|---|---|---|---|---|
| | CONTROL | SAMPLE 2 | SAMPLE 3 | SAMPLE 4 |
| Phenol | 1.0 | 3.4 | 1.6 | 2.2 |
| O-Cresol | 4.7 | 12.7 | 12.7 | 7.2 |
| 2,6-Xylenol | 78.4 | 76.9 | 77.8 | 76.7 |
| Mesitol | 15.4 | 5.9 | 7.4 | 13.4 |
| *Other | 0.5 | 0.2 | 0.5 | 0.5 |
| Selectivity | 83.1 | 92.7 | 90.8 | 84.7 |

*Other alkylated phenolics

The above results show that magnesium oxide (samples no. 2 and 3) resulting from the initial calcining of the magnesium carbonate followed by the steam treatment resulted in the highest selectivity with respect to maximizing the production of 2,6-xylenol and minimizing the production of mesitol. Catalyst activity also was maintained during the test period.

EXAMPLE 2

The procedure of example 1 was repeated with additional catalyst samples prepared in accordance with the sample 2 procedure using an initial calcination temperatures of 380° C. and 440° C. and a gas purge of dry nitrogen during calcination having 2% by weight oxygen at a rate of 1.1 liters/min. Steam temperatures of 380° C. and 440° were also used. Catalyst surface areas and selectivities were determined. The following results were obtained where selectivities are related to surface areas (SA)

| | SA | | Selectivities | |
|---|---|---|---|---|
| After Calcination | 380° C. (M²/g) 342 | 440° C. (M²/g) 257 | SA 221 Phenol 0.8 O-cresol 6.5 | 188 0.5 8.0 |
| After Steaming (380° C.) | 221 | 188 | xylenol 80.5 mesitol 11.8 other 0.4 | 82.6 8.5 0.4 |
| After Steaming (440) | 138 | 154 | Selectivity 86.8 SA 138 Phenol 3.8 O-cresol 12.0 xylenol 77.7 mesitol 6.0 other 0.5 Selectivity 92.3 | 90.3 154 2.5 16.9 74.5 5.5 0.6 92.4 |

The above results show as SA decreases, selectivity increases.

Although the above examples are directed to only a few of the many variables which can be used in the practice of the method of the present invention, it should be understood that the present invention is directed to the use of a much broader variety of conditions, such as the nature of the inert gas, duration of heating, and steaming, etc. which are set forth in the description preceding these examples.

What is claimed is:

1. A method for ortho-alkylating phenol, which comprises, effecting reaction between methanol and phenol at a temperature in a range from 350° C. to 550° C. in the presence of a magnesium oxide catalyst, where there is used from 3 to mols of methanol, per mol of phenol, and the magnesium oxide catalyst is the product obtained by
    (1) calcining magnesium carbonate at a temperature from about 350° C. to about 440° C. under a dry gas stream, selected from the class consisting of air, an inert gas, and an inert gas mixture having up to about 21% by weight oxygen to convert the magnesium carbonate to magnesium oxide and,
    (2) heating the calcined product of (1) at a temperature from 350° C. to 550° C. in the presence of steam until the surface area of the resulting magnesium oxide product achieves a predetermined value.

2. A method in accordance with claim 1, where the magnesium oxide catalyst is heated in the presence of nitrogen after it has been subjected to steaming.

3. A method in accordance with claim 1, where the surface area of the magnesium oxide catalyst is 100 M²/g to 200 M²/g.

4. A method in accordance with claim 1, where the magnesium carbonate is calcined in the presence of nitrogen.

5. A method in accordance with claim 1, where the dry gas stream used during calcining is air.

6. A method in accordance with claim 1, where the dry gas stream used during calcining is a mixture of nitrogen and 2% oxygen by weight.

* * * * *